United States Patent [19]
Akers

[11] Patent Number: 5,645,047
[45] Date of Patent: Jul. 8, 1997

[54] INHALATION MASK

[75] Inventor: Edward G. Akers, Granbury, Tex.

[73] Assignee: Stand-By Systems, Inc., Dallas, Tex.

[21] Appl. No.: 641,197

[22] Filed: Apr. 30, 1996

[51] Int. Cl.$^6$ ................................................. A62B 18/10
[52] U.S. Cl. .................... 128/201.28; 128/203.11; 128/205.24; 128/206.12; 128/207.12
[58] Field of Search ...................... 128/201.28, 203.11, 128/204.26, 205.24, 206.12, 206.15, 206.16, 207.12, 207.16, 207.17

[56] References Cited

U.S. PATENT DOCUMENTS 2,936,779  5/1960  Kindred ................................. 137/525
4,974,586  12/1990  Wandel et al. ...................... 128/207.12

Primary Examiner—Vincent Millin
Assistant Examiner—Robert N. Wieland
Attorney, Agent, or Firm—Timmons & Kelly

[57] ABSTRACT

A valve device (D) of the type used for a breathing apparatus (A) includes a mask section (10) that is adapted for mating with a desired subject (U), such as about a mouth and nose. An inlet tube (12) communicates a desired fluid, such as oxygen, into an interior chamber (16) of the mask (10). At least one plate assembly (18) has a thin, pliable outer section (20) to act as a flapper. A plate mount (22) retains the plate assembly (18), and has at least one pair of passages (24a and 24b) formed therethrough for communicating the fluid (14) out of the interior chamber (16) and an external fluid into the interior chamber (16) of the mask (10). Compatible portions (26a and 26b) of the pliable outer section (20) movably cover the passages (24a and 24b) in the plate mount (22) forming at least one inlet valve (28) that permits the flow of the external fluid into the interior chamber (16) and a second outlet valve (30) that permits the exhaust of combined fluid out of the interior chamber (16).

10 Claims, 3 Drawing Sheets

INHALATION MASK

BACKGROUND OF THE INVENTION

1. Technical Field

The invention relates to the field of valved devises and, more particularly, to a valved structure adapted for use as a breathing apparatus.

2. Background Art

Air masks used in conjunction with a breathing apparatus are well known in the art. Exemplary of such types of breathing apparatus include oxygen masks used for high altitude flying, emergency oxygen masks used for loss of pressure in aircraft, and medical oxygen therapy treatment units, both emergency and for hospital usage.

Oxygen masks are used with the breathing apparatus as an interface between the user and the source of gas or other desired fluid. The mask is fitted to the general contour of one's face about their mouth and nose, typically; Characteristic examples of such known oxygen masks used in oxygen therapy uses are those manufactured or sold by Hudson Oxygen-Therapy Sales Co. of Temecula, Calif., Life Support, Inc. of Melbourne, Fla., and Baxter Healthcare Corporation of Valencia, Calif.

As is generally the case with the above cited medical oxygen masks, such masks either do not include a valve regulating or controlling the passage of the gas or include a single valve that permits fluid flow in a single direction.

In U.S. Pat. No. 2,936,779 (Kindred) a mask having a flapper valve is disclosed. The flapper valve as taunt in Kindred permits the flow of the gas or other desired fluid in a single direction and forms a seal against the flow of the fluid in a reverse direction or when the flow ceases.

While the above cited references introduce and disclose a number of noteworthy advances and technological improvements within the art, none completely fulfills the specific objectives achieved by this invention.

DISCLOSURE OF INVENTION

In accordance with the present invention, a valve device of the type used for a breathing apparatus includes a mask section that is adapted for mating with a desired subject, such as about a mouth and nose. An inlet tube communicates a desired fluid, such as oxygen, into an interior chamber of the mask. At least one plate assembly has a thin, pliable outer section to act as a flapper. A plate mount retains the plate assembly, and has at least one pair of passages formed therethrough for communicating the fluid into and out of the interior chamber of the mask. Compatible portions of the pliable outer section movably cover the passages in the plate mount forming at least one inlet valve that permits the flow of the fluid into the interior chamber and a second outlet valve that permits the flow of the fluid out of the interior chamber.

These and other objects, advantages and features of this invention will be apparent from the following description taken with reference to the accompanying drawings, wherein is shown the preferred embodiments of the invention.

BRIEF DESCRIPTION OF THE DRAWINGS

A more particular description of the invention briefly summarized above is available from the exemplary embodiments illustrated in the drawing and discussed in further detail below. Through this reference, it can be seen how the above cited features, as well as others that will become apparent, are obtained and can be understood in detail. The drawings nevertheless illustrate only typical, preferred embodiments of the invention and are not to be considered limiting of its scope as the invention may admit to other equally effective embodiments.

MODE(S) FOR CARRYING OUT THE INVENTION

Figure 1:
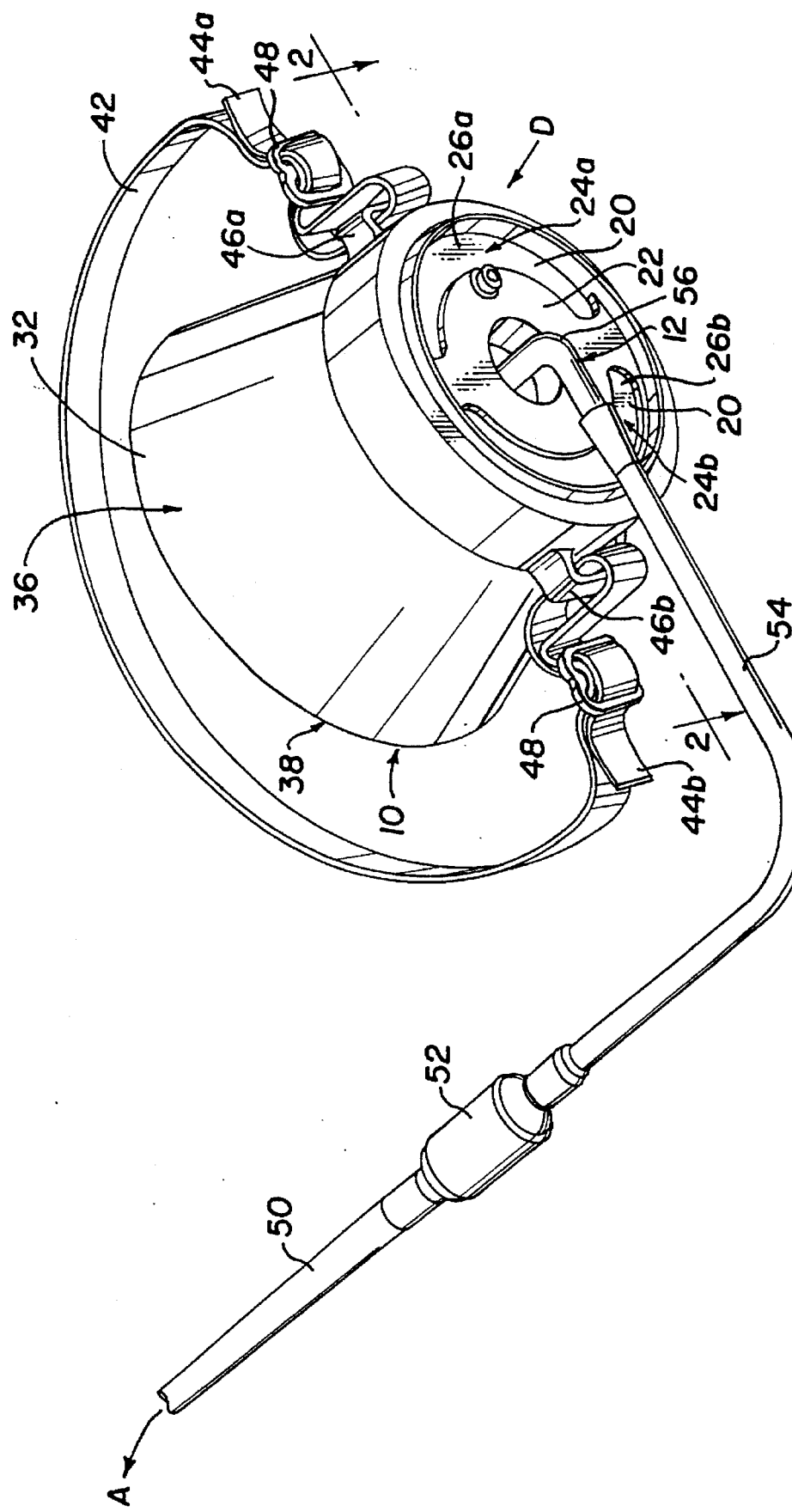
FIG. 1 is a perspective view of the inhalation mask with strap and air hose attached in accordance with the present invention.

So that the manner in which the above recited features, advantages and objects of the present invention are attained can be understood in detail, more particular description of the invention; briefly summarized above, may be had by reference to the embodiment thereof that is illustrated in the appended drawings. In all the drawings, identical numbers represent the same elements.

A valve device D of the type used for a breathing apparatus A includes a mask section 10 that is adapted for mating with a desired subject U, such as about a mouth and nose. An inlet tube 12 communicates a desired first in-flowing fluid 14, such as oxygen, into an interior chamber 16 of the mask 10. At least one plate assembly 18 has a thin, pliable outer section 20 to act as a flapper. A plate mount 22 retains the plate assembly 18, and has at least one pair of passages, 24a and 24b respectively, formed therethrough for communicating the fluid 14 out of the interior chamber 16 and an external second fluid, such as the surrounding or ambient air, into the interior chamber 16 of the mask 10. Compatible portions, 26a and 26b respectively, of the pliable outer section 18 movably cover the passages 24a and 24b in the plate mount 22 to form at least one inlet valve 28 that permits the flow of the second external fluid into the interior chamber 16 and a second outlet valve 30 that permits the exhaust flow of the combined in-flowing first fluid 14 and second external fluid out of the interior chamber 16.

The mask section 10 is a known type of an enclosure to fit or form about a user's mouth and nose. Typically, such mask sections are composed of a thin pliable sheet-like material, such as a type of plastic or rubber. The mask section may be formed with a skit member 32 into a general frustum shape segment 36 between a base opening 38 and a top 40. The skit 32 may optionally include a nose portion 34 that protrudes from the frustum or frusto-conical segment 36 to adapt to or more closely fit about the user's nose. See FIG. 5. Alternatively, the mask section 10 may be any known shape utilized in air or breathing masks.

The hollow inlet tube 12 communicates the desired fluid or gas 14 from a breathing apparatus or gas or air supply A into the interior 16 or the mask. Optionally, the inlet tube 12 may be composed of a tubular first section 50 leading from the breathing apparatus A. The first tubular section 50 may be connected to a joint or coupling 52 that may be of any known type such as a quick-coupling connector or a valved connector that passes the fluid therethrough. The coupling 52 is connected to a second hollow or tubular segment 54 that is further connected to a hollow elbow tube 56 leading into the interior 16 of the mask 10.

The first end 58 of the elbow tube 56 has an opening 59 located in a chamber 60 in the top 40 of the mask section 10 and in proximity to an opening 62 formed through a plate 64 separating the interior 16 of the mask 10 from the chamber 60. Thus, the desired fluid or gas is introduced into the first tubular segment 50 and is communicated through the coupling 52, the second tube 54, elbow 56 and through the opening 58 into the mask's interior 16 for application near the user's mouth and nose when positioned in the present inhalation mask.

Optionally, both ends of the elbow 56 may be formed with a shoulder 57. The shoulder 57 located near the first end 58 of the elbow 56 may be used to secure the elbow end within or from pulling out of the chamber 60. The shoulder 57 located near the opposite end of the elbow 56 may be used for a pressure fit of the end of the tube 54.

The valve portion of the present inhalation mask includes the plate assembly 18 secured within a plate mount 22. A thin, outer portion 20 of the mounted plate assembly 18 acts as a flapper type valve in conjunction with at least a pair of passages 24a and 24b formed through the plate mount 22.

The plate mount 22 is generally composed of a rigid plastic material formed into an interior ring 66 and a compatible outer ring 68 that binds a portion of the skirt 32 between the two rings 66 and 68. The inner ring includes a cup portion 70 having the opening 62. A compatible cup portion 72 is formed in the outer FIG. 68 and is engaged or nests within inner ring cup portion 70 forming chamber 60 therebetween.

Figure 3:
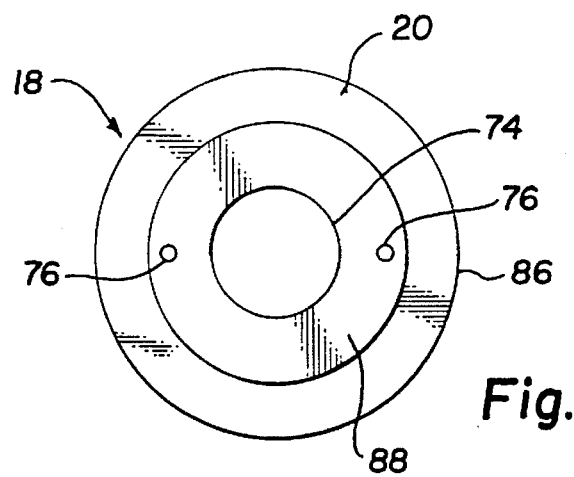
FIG. 3 is a top view of a circular version of the plate assembly.
Figure 4:
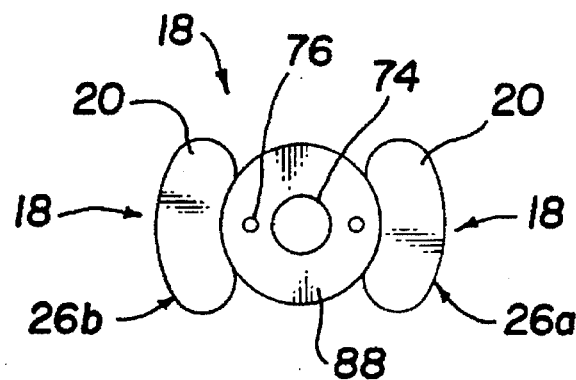
FIG. 4 is a top view of an alternative shaped plate assembly.

The plate assembly 18 is preferably formed in a circular disk shape as is shown in FIG. 3 having a center hole 74 for mounting about the outer ring cup 72 when the plate assembly 18 is secured between inner ring 66 and outer ring 68. Guide holes 76 formed in plate assembly 18 and cooperating guide or locking pins 78 with inner ring 66 are used to orient and for proper placement of the plate assembly 18. Alternatively, a "bone" shaped plate assembly 18 is shown in FIG. 4 with the flaps 26a and 26b in the shape of lobes extending from the center portion 88. There are at least two lobes that correspond in number and shaped to the passages 24a and 24b.

Referring now to an outlet valve 30 of the present invention, holes are formed in both the inner ring 66 and the outer ring 68 such that the pairs of holes are aligned with one above the other forming an outlet passage 24a into the interior 16 of the mask section 10 when the inner ring 66 and outer ring 68 of the plate mount 22 are assembled. The hole 80a in the outer ring 68 is slightly larger than the comparable hole 82a that is formed in the inner ring 66. The difference in sizes of the two holes in the pair creates a shoulder 84a that acts as a stop for a free or movable outer edge 86 to prevent outlet portion 26a of the mounted or installed plate assembly 18 from moving toward the interior 16 of the mask 10 in the outlet passage 24a. In this way the outlet portion 26a substantially blocks the flow of any fluid from the outside or exterior of the mask through the outlet passage 24a into the interior 16 thereby creating a substantially one way outlet valve 28. However, the free outlet portion 26a permits the flow of the fluid out from the interior 16.

Similarly, an inlet valve 28 has hole 80b formed in outer ring 68 slightly smaller than the comparable hole 82b formed in the inner ring 66. This difference in size creates a shoulder 84b in the inlet passage 24b. The shoulder 84b acts as a stop to prevent an inlet portion 26b of the installed plate assembly 18 from moving away from the interior 16 of the mask 10 in the inlet passage 24b, while permitting the flow of the external second fluid into the interior 16.

Figure 2:
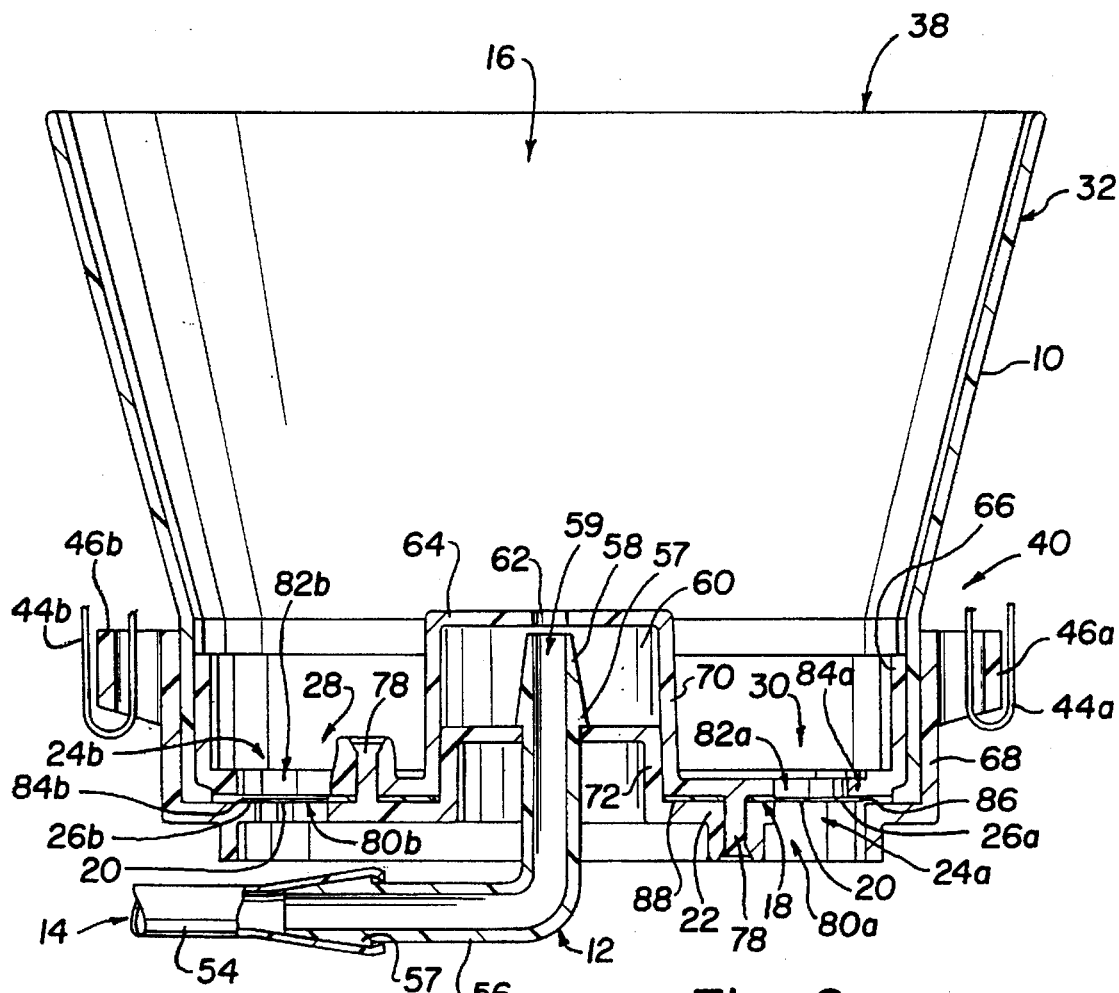
FIG. 2 is a section view of the mask section and plate assembly and mount taken along line 2—2 of FIG. 1.

The plate assembly 18 is composed of a pliable material, such as polyethylene or other rubber or plastic type composition. Preferably, the outer section 20 of the pliable plate assembly 18 has a thickness that is less than the thickness of an interior section 88 of the plate assembly 18. Desirably, the outer section 20 of a polyethylene plate assembly 18 has a minimum thickness, for example between 0.05 and 0.200 inches thick. See the cross section of the movable outer section 20 in FIG. 2. The type of material and the thickness are factors in the amount of force needed to actuate the flapper valve formed in the present valve device D to permit normal breathing.

When the mask section is in place about a user's mouth and nose, as desired, the interior chamber 16 is defined by the space within the circumference of the skirt member 32, the top of the mask section including the plate mount 22 with installed plate assembly 18, and the front of the user's face.

Figure 5:
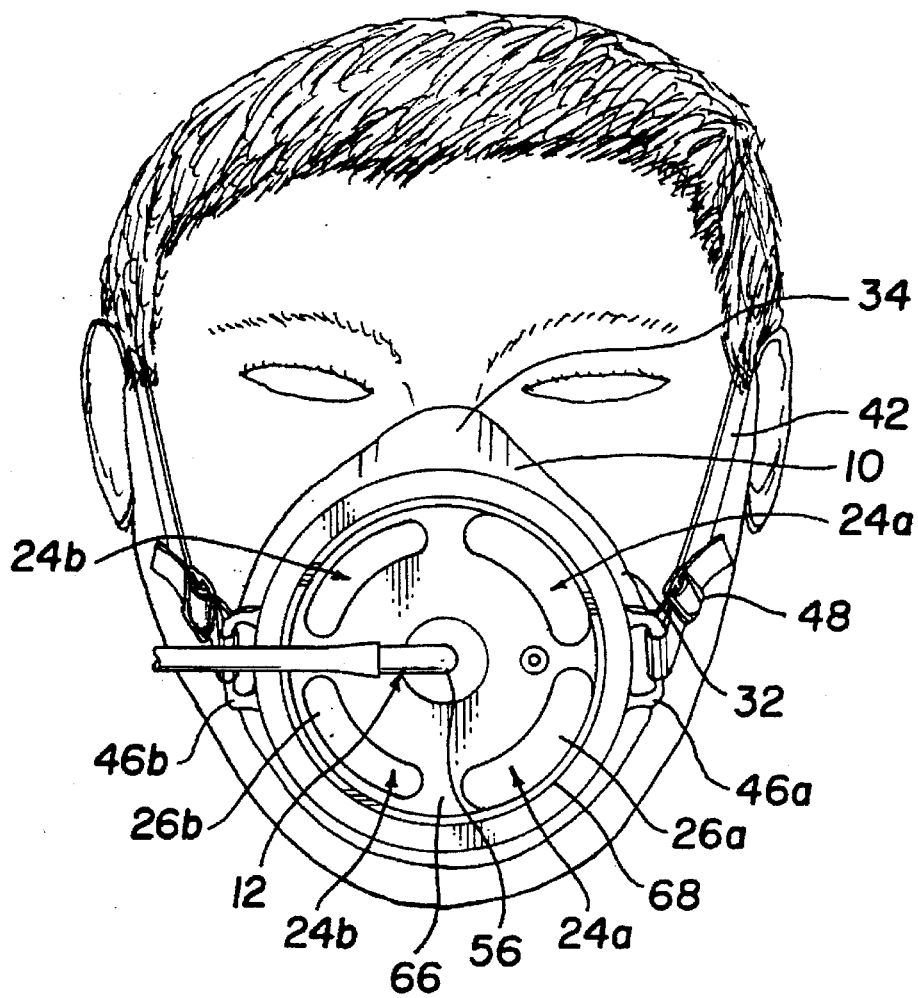
FIG. 5 is a frontal view of the inhalation mask of the present invention as worn by a user.

An adjustable headband 42 is desirably attached to the top 40 of the mask section 10 to secure the inhalation mask about the user's head as shown in FIG. 5. Typically, the two ends 44a and 44b of the headband or strap 42 pass through or are looped about ears or rings 46a and 46b, respectively, and are further secured with adjustable locking loop members 48 on each end 44a and 44b.

Operation

In operation of the present invention the user U first secures the inlet tube 12 to the breathing apparatus or air supply A and places the mask section 10 about their mouth and nose, as desired, utilizing the headband 42. The flow of the first fluid or gas 14 is started through the inlet tube 12 and is communicated out through the hole 59 in the elbow 56 into the chamber 60. The first gas 14 fills the chamber 60 and vents through hole 62 into the interior 16 of the mask 10.

Upon an exhalation cycle by the user U into the interior 16 of the mask 10, the fluid or air pressure in the interior 16 of the mask 10 increases. Upon reaching the controlled pressure level in the interior 16, the outer edge 86 of the exit flap 26a is pushed away from the shoulder 84a creating an opening through which the inner atmosphere in the interior 16 of the mask 10 vents to the exterior or outside of the mask 10 to mix with the exterior or second fluid or gas.

Similarly, upon an inhalation cycle by the user U wearing the mask, the air pressure in the interior 16 of the mask 10 decreases. Upon reaching the controlled pressure drop in the interior 16, the outer edge 86 of the entrance flap 26b of the inlet passage 24b is moved away from the shoulder 84b creating an opening through which the external or second fluid or gas enters into the interior 16 of the mask 10 to mix with the first fluid or gas 14 that is introduced from the inlet tube 12.

The foregoing disclosure and description of the invention are illustrative and explanatory thereof; and various changes in the size, shape and materials, as well as in the details of the illustrated construction may be made without departing from the spirit of the invention.

I claim:

1. An valve device comprising:
   a mask section adapted for mating with a desired subject;
   means for introducing a desired fluid into an interior chamber of said mask section;

at least one plate assembly having a thin, pliable outer section;

plate mounting means with said mask section for retaining said plate assembly, said plate mounting means having at least one pair of passages formed therethrough for communicating the fluid out of the interior chamber and an external fluid into the interior chamber of said mask section;

compatible portions of said pliable outer section movably covering said passages in the plate mounting means forming at least one inlet valve permitting the flow of the external fluid into the interior chamber of said mask section and a second outlet valve permitting the flow of fluid out of the interior chamber of said mask section.

2. The invention of claim 1 wherein said plate mounting means is formed with at least one passage with said inlet valve having lip means to retard the flexing of said compatible portion of the pliable outer section in an outward direction and at least one passage with said outlet valve having lip means to retard the flexing of said compatible portion of the pliable outer section in an inward direction.

3. The invention of claim 1 wherein said compatible portions of said pliable outer section are normally in a closed position closing said passages in the plate mounting means to the passage of a fluid.

4. The invention of claim 1 wherein said mask section includes a pliable skirt.

5. The invention of claim 1 wherein said mask section essentially forms a frustum.

6. The invention of claim 1 wherein said plate assembly is a disk.

7. The invention of claim 1 wherein said plate assembly is polyethylene.

8. The invention of claim 7 wherein said compatible portions of said pliable outer section of the plate assembly has a thickness less than the thickness of an interior section of the plate assembly.

9. The invention of claim 7 wherein said compatible portions of said pliable outer section of the plate assembly has a desired thickness between 0.01 and 0.02 inches.

10. The invention of claim 7 wherein said compatible portions of said pliable outer section of the plate assembly has a desired thickness to permit normal breathing.

* * * * *